US008592477B2

(12) United States Patent
Wolff et al.

(10) Patent No.: US 8,592,477 B2
(45) Date of Patent: Nov. 26, 2013

(54) POLYMORPHIC FORM OF ROTIGOTINE AND PROCESS FOR PRODUCTION

(75) Inventors: Hans-Michael Wolff, Monheim (DE); Luc Quere, Sombreffe (BE); Jens Riedner, Monheim (DE)

(73) Assignee: UCB Pharma GmbH, Monheim (DE)

( * ) Notice: Subject to any disclaimer, the term of this patent is extended or adjusted under 35 U.S.C. 154(b) by 309 days.

(21) Appl. No.: 12/744,989

(22) PCT Filed: Nov. 25, 2008

(86) PCT No.: PCT/EP2008/066137
§ 371 (c)(1),
(2), (4) Date: Aug. 27, 2010

(87) PCT Pub. No.: WO2009/068520
PCT Pub. Date: Jun. 4, 2009

(65) Prior Publication Data
US 2010/0311806 A1    Dec. 9, 2010

Related U.S. Application Data

(60) Provisional application No. 60/990,721, filed on Nov. 28, 2007.

(30) Foreign Application Priority Data

Nov. 28, 2007  (EP) .................................. 07121795
Oct. 14, 2008  (EP) .................................. 08166576

(51) Int. Cl.
*A61K 31/381*   (2006.01)
*C07D 333/20*   (2006.01)

(52) U.S. Cl.
USPC ............................................ 514/438; 549/75

(58) Field of Classification Search
USPC ............................................ 514/438; 549/75
See application file for complete search history.

(56) References Cited

U.S. PATENT DOCUMENTS

| | | | |
|---|---|---|---|
| 4,320,148 A | 3/1982 | DeMarinis | 424/330 |
| 4,540,691 A | 9/1985 | Horn | 514/211 |
| 5,071,875 A | 12/1991 | Horn et al. | 514/613 |
| 5,151,446 A | 9/1992 | Horn et al. | 514/617 |
| 5,177,112 A | 1/1993 | Horn | 514/65 |
| 5,214,156 A | 5/1993 | Anderson et al. | 549/75 |
| 5,382,596 A | 1/1995 | Sleevi et al. | 514/459 |
| 5,486,611 A | 1/1996 | Lin et al. | 546/62 |
| 5,545,755 A | 8/1996 | Lin et al. | 564/428 |
| 6,331,636 B1 | 12/2001 | Romero et al. | 548/235 |
| 6,372,920 B1 | 4/2002 | Minaskanian et al. | 549/75 |
| 6,620,429 B1 | 9/2003 | Müller | 424/449 |
| 6,884,434 B1 | 4/2005 | Muller et al. | 424/487 |
| 7,309,497 B2 | 12/2007 | Rimpler et al. | 424/422 |
| 7,413,747 B2 | 8/2008 | Mueller et al. | 424/448 |
| 2003/0026830 A1 | 2/2003 | Lauterback et al. | 424/449 |
| 2003/0027793 A1 | 2/2003 | Lauterback et al. | 514/63 |
| 2003/0166709 A1 | 9/2003 | Rimpler et al. | 514/447 |
| 2004/0034083 A1 | 2/2004 | Stephenson et al. | 514/406 |
| 2004/0048779 A1 | 3/2004 | Schollmayer et al. | 514/2 |
| 2004/0081683 A1 | 4/2004 | Schacht et al. | 424/449 |
| 2004/0116537 A1 | 6/2004 | Li et al. | 514/663 |
| 2004/0137045 A1 | 7/2004 | Breitenbach et al. | 424/449 |
| 2004/0209861 A1 | 10/2004 | Benavides et al. | 514/210.01 |
| 2005/0033065 A1 | 2/2005 | Mueller et al. | 549/74 |
| 2005/0079206 A1 | 4/2005 | Schacht et al. | 424/449 |
| 2005/0175678 A1 | 8/2005 | Breitenbach | 424/448 |
| 2005/0197385 A1 | 9/2005 | Scheller et al. | 514/438 |
| 2005/0260254 A1 | 11/2005 | Breitenbach et al. | 424/449 |
| 2006/0216336 A1 | 9/2006 | Wolff | 424/448 |
| 2006/0263419 A1 | 11/2006 | Wolff | 424/448 |
| 2007/0072917 A1 | 3/2007 | Scheller et al. | 514/357 |
| 2007/0093546 A1 | 4/2007 | Scheller et al. | 514/447 |
| 2007/0191308 A1 | 8/2007 | Kramer | 514/60 |
| 2007/0191470 A1 | 8/2007 | Scheller | 514/438 |
| 2007/0197480 A1 | 8/2007 | Scheller et al. | 514/114 |
| 2008/0008748 A1 | 1/2008 | Beyreuther et al. | 424/449 |
| 2008/0138389 A1 | 6/2008 | Muller et al. | 424/448 |
| 2008/0146622 A1 | 6/2008 | Scheller et al. | 514/357 |
| 2008/0274061 A1 | 11/2008 | Schollmayer et al. | 424/45 |
| 2009/0143460 A1 | 6/2009 | Wolff et al. | 514/438 |
| 2011/0104281 A1 | 5/2011 | Beyreuther et al. | 424/486 |
| 2011/0165247 A1 | 7/2011 | Breitenbach | 424/486 |
| 2012/0101146 A1 | 4/2012 | Bouwstra et al. | 514/438 |
| 2012/0215185 A1 | 8/2012 | Schacht et al. | 604/290 |
| 2012/0322845 A1 | 12/2012 | Wolff et al. | 541/438 |

FOREIGN PATENT DOCUMENTS

| | | |
|---|---|---|
| CA | 2532804 | 2/2005 |
| CA | 2532859 | 2/2005 |
| CA | 2547820 | 6/2005 |
| CA | 2546797 | 7/2005 |
| CA | 2547645 | 7/2005 |

(Continued)

OTHER PUBLICATIONS

Barfknecht et al. (1973) J. Med. Chem. 16 (7):804-808.
DeNinno et al. (2001) J. Org. Chem 66:6988-6993.
EMEA (2006) Scientific discussion (Neupro), www.emea.europa.eu/humandocs/PDFs/EPAR/neupro/062606ene.pdf, 40 pp.
Hadgraft (2003) "Trans(dermal) delivery, present and future perspectives," The Drug Delivery Companies Report, Spring/Summer 2003, 6 pp.
Nugroho et al. (2004) openaccess.leidenuniv.nl/bitstream/1887/2316/8/03.pdf, pp. 37-53 (adapted from Pharm. Res. 21:844-850.
Sarges et al. (1973) J. Med. Chem. 16(9):1003-1011.
Sonesson et al. (1995) J. Med. Chem. 38:1319-1329.
Wikström et al. (1985) J. Med. Chem. 28:215-225.
Office Action, dated Sep. 19, 2011 issued in U.S. Appl. No. 12/324,166.
Office Action, dated Oct. 16, 2008 issued in U.S. Appl. No. 10/587,637.

(Continued)

*Primary Examiner* — Taofiq A Solola
(74) *Attorney, Agent, or Firm* — Harness, Dickey & Pierce, P.L.C.

(57) ABSTRACT

The present invention relates to a novel polymorphic form of Rotigotine characterized by at least one of the following X-ray powder diffraction peaks: 12.04, 13.68, 17.72 and 19.01±0.2 (°2θ), measured with a Cu—K$_\alpha$ irradiation (1.54060), and a process for production thereof, which is useful for the manufacture of a stable medicament for treating or alleviating symptoms of Parkinson's Disease and other dopamine-related disorders.

5 Claims, 10 Drawing Sheets

(56) References Cited

FOREIGN PATENT DOCUMENTS

| | | | |
|---|---|---|---|
| CA | 2559683 | 10/2005 | |
| CN | 1731995 | 2/2006 | ........... A61K 31/381 |
| WO | WO 89/12445 | 12/1989 | ............ A61K 31/34 |
| WO | WO 93/00313 | 1/1993 | |
| WO | WO 94/26703 | 11/1994 | |
| WO | WO 99/49852 | 10/1999 | ............... A61K 9/70 |
| WO | WO 02/15903 | 2/2002 | ............ A61K 47/14 |
| WO | WO 02/089777 | 11/2002 | |
| WO | WO 03/012137 | 2/2003 | ............... C12Q 1/68 |
| WO | WO 03/092677 | 11/2003 | ............... A61K 9/70 |
| WO | WO 2004/039320 | 5/2004 | |
| WO | WO 2004/050083 | 6/2004 | |
| WO | WO 2004/058247 | 7/2004 | ........... A61K 31/381 |
| WO | WO 2005/009424 | 2/2005 | ........... A61K 31/135 |
| WO | WO 2005/063236 | 7/2005 | |
| WO | WO 2005/063237 | 7/2005 | ........... A61K 31/381 |
| WO | WO 2005/092331 | 10/2005 | ........... A61K 31/381 |
| WO | WO 2006/069030 | 6/2006 | |
| WO | WO 2008/146284 | 12/2008 | ........... A61K 31/381 |

OTHER PUBLICATIONS

Office Action, dated Apr. 1, 2009 issued in U.S. Appl. No. 10/587,637.
Office Action, dated Sep. 2, 2009 issued in U.S. Appl. No. 10/587,637.
Office Action, dated Jun. 7, 2010 issued in U.S. Appl. No. 10/587,637.
Brittain, (1999) "Methods for the characterization of polymorphs and solvates" Polymorphism in Pharmaceutical Solids 227-278.
Chaudhuri, (2008) "Crystallisation within transdermal rotigotine patch: is there cause for concern" Expert Opin. Drug Deliv, 5(11):1169-1171.
International Search Report, PCT/EP2008/066137, dated Sep. 24, 2009.
The Cambridge Crystallographic Data Centre; "The Cambridge Structural Database" XP007906502. Database Accession No. 163602, 2001.
Van der Weide, et al. (1988) "The enantiomers of the D-2 dopamine receptor agonist N-0437 discriminate between pre- and postsynaptic dopamine receptors." Eur J Pharmacol 146:319-326.
International Search Report dated Aug. 14, 2009 issued in PCT/EP2008/066137.
International Preliminary Report on Patentability dated Jun. 1, 2010 issued in PCT/EP2008/066137.
Office Action dated Sep. 21, 2006 issued in U.S. Appl. No. 10/429,283.
Office Action dated Mar. 23, 2007 issued in U.S. Appl. No. 10/713,424.
Office Action dated Aug. 17, 2007 issued in U.S. Appl. No. 10/623,864.
Office Action dated Sep. 13, 2007 issued in U.S. Appl. No. 10/936,620.
Office Action dated Sep. 14, 2007 issued in U.S. Appl. No. 10/713,424.
Office Action dated Jan. 8, 2008 issued in U.S. Appl. No. 10/429,283.
Office Action dated Jan. 23, 2008 issued in U.S. Appl. No. 11/931,666.
Office Action dated May 1, 2008 issued in U.S. Appl. No. 10/936,620.
Office Action dated Jun. 25, 2008 issued in U.S. Appl. No. 10/713,424.
Office Action dated Sep. 10, 2008 issued in U.S. Appl. No. 10/429,283.
Office Action dated Dec. 10, 2008 issued in U.S. Appl. No. 10/565,713.
Office Action dated Feb. 2, 2009 issued in U.S. Appl. No. 10/627,990.
Office Action dated Feb. 19, 2009 issued in U.S. Appl. No. 10/713,424.
Office Action dated Mar. 6, 2009 issued in U.S. Appl. No. 10/517,157.
Office Action dated Mar. 30, 2009 issued in U.S. Appl. No. 10/429,283.
Office Action dated Apr. 7, 2009 issued in U.S. Appl. No. 10/565,713.
Office Action dated Aug. 5, 2009 issued in U.S. Appl. No. 10/593,964.
Office Action dated Aug. 18, 2009 issued in U.S. Appl. No. 10/627,990.
Office Action dated Oct. 15, 2009 issued in U.S. Appl. No. 10/139,894.
Office Action dated Oct. 23, 2009 issued in U.S. Appl. No. 10/565,699.
Office Action dated Dec. 7, 2009 issued in U.S. Appl. No. 10/565,713.
Office Action dated Dec. 23, 2009 issued in U.S. Appl. No. 10/429,283.
Office Action dated Apr. 27, 2010 issued in U.S. Appl. No. 10/627,990.
Office Action dated May 27, 2010 issued in U.S. Appl. No. 10/565,699.
Office Action dated Jun. 9, 2010 issued in U.S. Appl. No. 11/931,762.
Office Action dated Aug. 3, 2010 issued in U.S. Appl. No. 10/517,157.
Office Action dated Aug. 16, 2010 issued in U.S. Appl. No. 11/239,701.
Office Action dated Aug. 31, 2010 issued in U.S. Appl. No. 10/623,864.
Office Action dated Oct. 1, 2010 issued in U.S. Appl. No. 10/429,283.
Office Action dated Jan. 4, 2011 issued in U.S. Appl. No. 10/627,990.
Office Action dated Feb. 14, 2011 issued in U.S. Appl. No. 10/565,699.
Office Action dated May 4, 2011 issued in U.S. Appl. No. 10/429,283.
Office Action dated May 12, 2011 issued in U.S. Appl. No. 10/623,864.
Office Action dated May 12, 2011 issued in U.S. Appl. No. 11/239,701.
Office Action dated May 24, 2011 issued in U.S. Appl. No. 10/140,096.
Office Action dated Jul. 22, 2011 issued in U.S. Appl. No. 12/324,166.
Office Action dated Oct. 18, 2011 issued in U.S. Appl. No. 11/239,701.
Office Action dated Oct. 19, 2011 issued in U.S. Appl. No. 10/139,894.
Office Action dated Oct. 31, 2011 issued in U.S. Appl. No. 10/627,990.
Office Action dated Nov. 8, 2011 issued in U.S. Appl. No. 10/565,699.
Office Action dated Dec. 2, 2011 issued in U.S. Appl. No. 10/140,096.
Office Action dated Feb. 3, 2012 issued in U.S. Appl. No. 10/429,283.
Office Action dated Jul. 12, 2012 issued in U.S. Appl. No. 13/457,848.
Office Action dated Aug. 15, 2012 issued in U.S. Appl. No. 13/020,414.
Office Action dated Dec. 18, 2012 issued in U.S. Appl. No. 10/140,096.
Office Action dated Dec. 19, 2012 issued in U.S. Appl. No. 10/139,894.

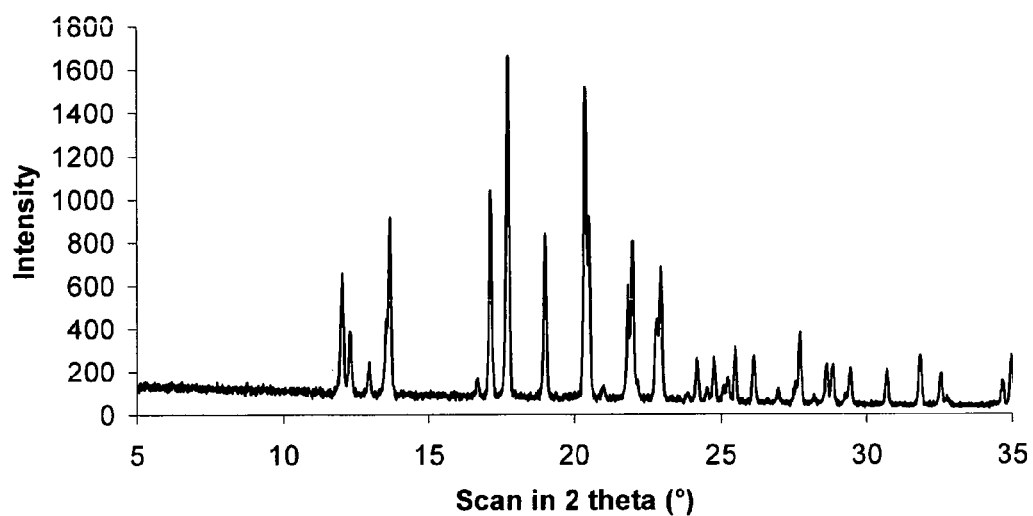
Figure 1  Experimental powder X-ray diffractogram of novel polymorphic form (II) of Rotigotine

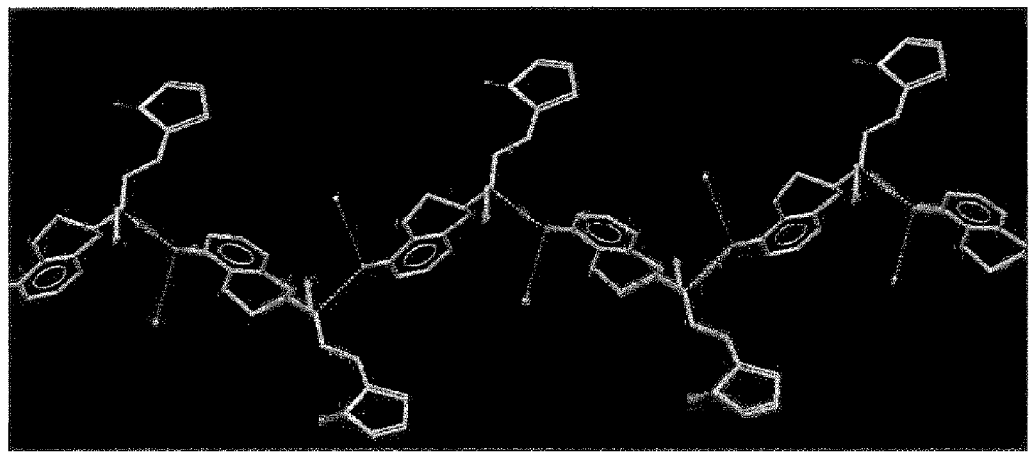
Figure 2  H-bonded polymeric (Zig-Zag) chain of Rotigotine molecules in novel polymorphic form (II) crystals

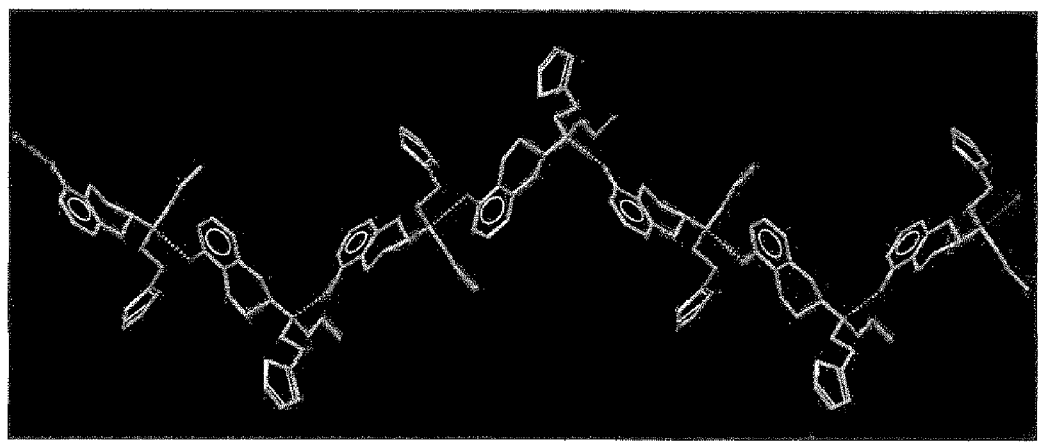
Figure 3  H-bonded polymeric (Zig-Zag) chain of Rotigotine molecules in polymorphic form (I) crystals

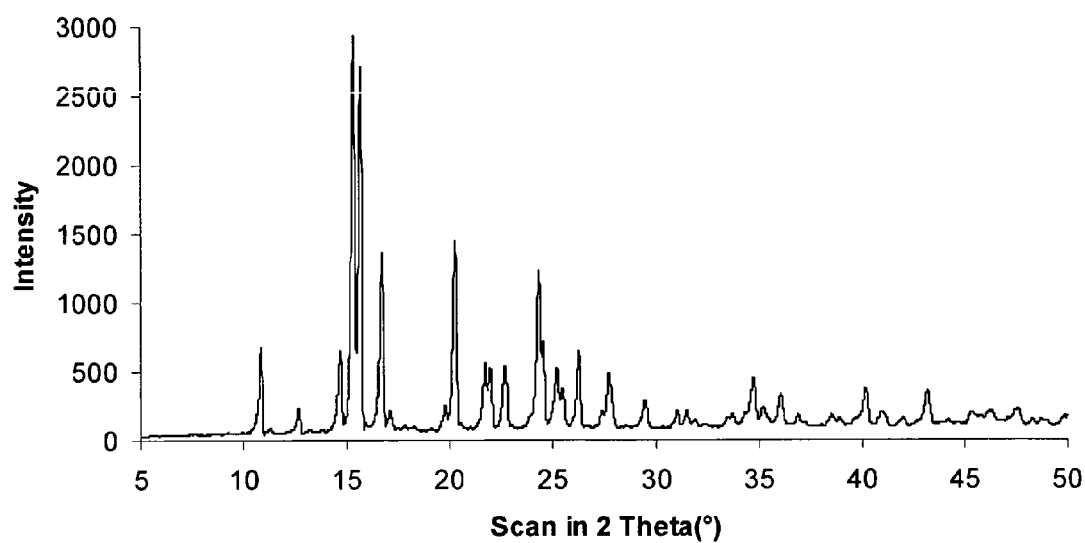
Figure 4 Experimental powder X-ray diffractogram of polymorphic form (I) of Rotigotine

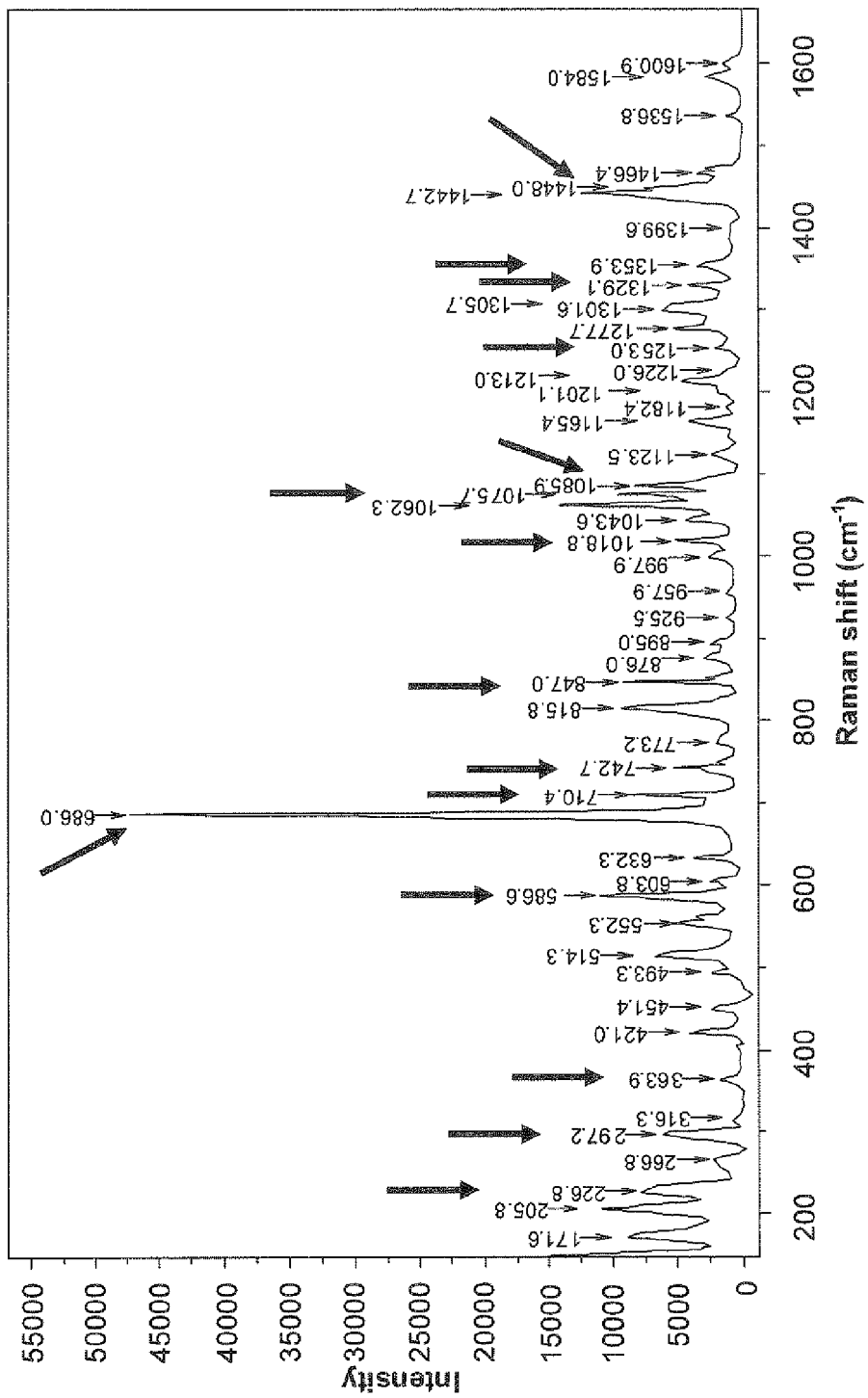
Figure 5  Raman spectrum of novel polymorphic form (II) of Rotigotine

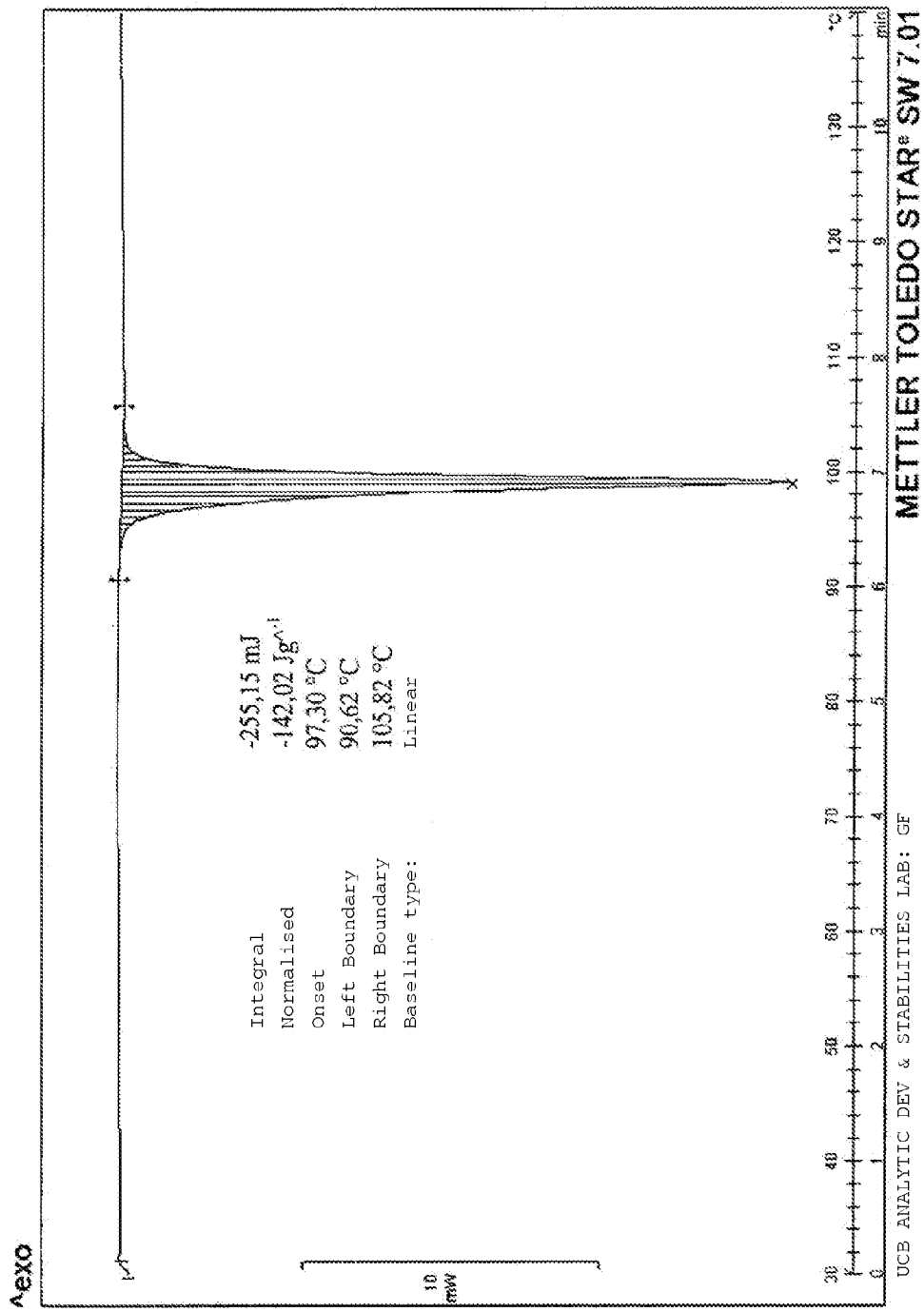
Figure 7 DSC thermogram of novel polymorphic form (II) of Rotigotine (batch 7769396).

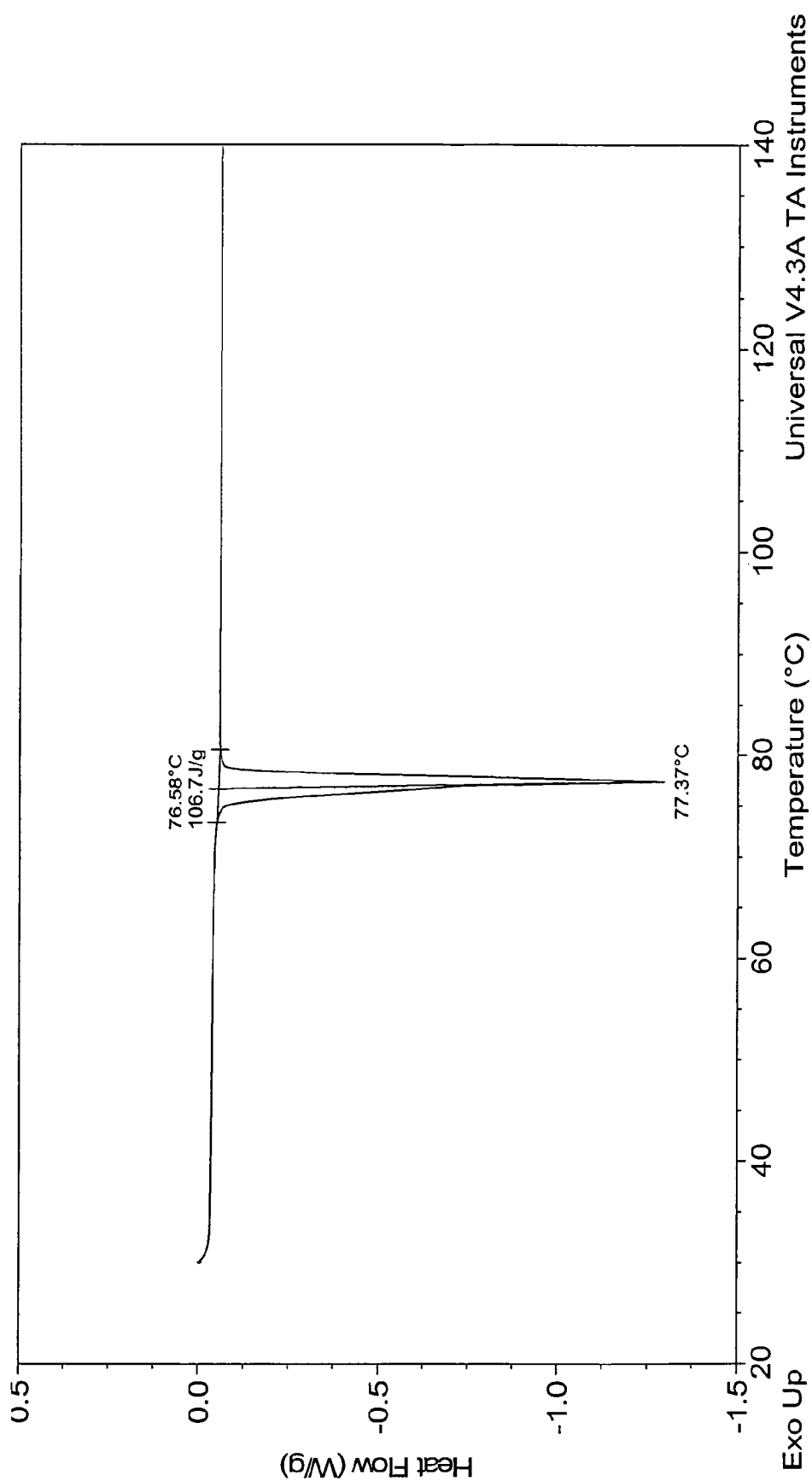
Figure 8  DSC thermogram of polymorphic form (I) of Rotigotine (batch 1608726).

POLYMORPHIC FORM OF ROTIGOTINE AND PROCESS FOR PRODUCTION

CROSS-REFERENCE TO RELATED APPLICATIONS

The present application is the national stage under 35 U.S.C. §371 of International Patent Application No. PCT/EP2008/066137 filed on 25 Nov. 2008, which claims the priority of each of European Patent Application No. EP 07 121 795.4 filed on 28 Nov. 2007, U.S. Provisional Application Ser. No. 60/990,721 filed on 28 Nov. 2007, and European Patent Application No. EP 08 166 576.2 filed on 14 Oct. 2008. Each of the above referenced applications is incorporated herein by reference in its entirety.

FIELD OF THE INVENTION

The present invention relates to a novel polymorphic form (form II) of Rotigotine and a process for production thereof, which form is useful for the manufacture of a stable medicament for treating or alleviating symptoms of Parkinson's Disease and other dopamine-related disorders.

TECHNICAL BACKGROUND

Rotigotine is the International Non-Proprietary Name (INN) of the compound (−)-5,6,7,8-tetrahydro-6-[propyl-[2-(2-thienyl)ethyl]-amino]-1-naphthalenol having the structure shown below

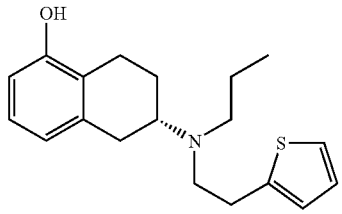 [SMILES: CCCN(CCc1cccs1)[C@H]1CCc2c(O)cccc2C1]

Rotigotine is a non-ergolinic D1/D2/D3 dopamine agonist that resembles dopamine structurally and has a similar receptor profile but a higher receptor affinity.

In contrast to other non-ergolinic dopamine agonists, Rotigotine has significant D1 activity, which may contribute to a greater physiological action.

In contrast to ergolinic compounds, Rotigotine has a very low affinity for 5 $HT_2B$ receptors and thus a low risk of inducing fibrosis.

Actions on non-dopaminergic receptors (such as 5-$HT_1A$ agonism and $A_{2B}$ antagonism) may contribute to other beneficial effects, such as antidyskinetic activity, neuroprotective activity and antidepressive effects.

Rotigotine is disclosed as active agent for treating patients suffering from Parkinson's disease (described in WO 2002/089777), Parkinson's plus syndrome (described in WO 2005/092331), depression (described in WO 2005/009424) and the restless-legs syndrome (described in WO 2003/092677) as well as for the treatment or prevention of dopaminergic neuron loss (described in WO 2005/063237).

Known pharmaceutical compositions containing Rotigotine comprise a transdermal therapeutic system (TTS) (described in WO 99/49852), a depot form (described in WO 02/15903), an iontophoretic device (described in WO 2004/050083) and an intranasal formulation (described in WO 2005/063236).

Each of the above cited publications is incorporated by reference in its entirety herein.

One crystalline form of Rotigotine is already known and will hereinafter be designated as polymorphic form (I).

Surprisingly a further crystalline form of Rotigotine (polymorphic form (II)) has now been identified and found to show a greatly enhanced thermodynamic stability and an improved shelf-life as well as a cubic crystal shape that represents an advantage over the needle like particles of polymorphic form (I) regarding its handling properties such as filtering properties, flowability, electrostatic behaviour, etc.

The discovery of a second crystalline Rotigotine polymorph is especially astonishing as Rotigotine is a commercial drug that has been known since the mid eighties and has been well investigated over the past decade. Furthermore, no indication for the presence of a second crystalline Rotigotine polymorph was observed in a first polymorphism screening that was earlier conducted during formulation development.

SUMMARY OF THE INVENTION

The present invention provides a novel polymorphic form (form II) of Rotigotine ((−)-5,6,7,8-tetrahydro-6-[propyl-[2-(2-thienyl) ethyl]-amino]-1-naphthalenol).

The novel polymorphic form of Rotigotine according to the present invention has at least one of the following characteristics:
  a X-ray powder diffraction spectrum comprising a peak at least at one of the following °2θ angles (±0.2): 12.04, 13.68, 17.72 and/or 19.01, measured with Cu—$K_\alpha$ irradiation (1.54060 Å);
  a Raman spectrum comprising at least one peak at the following wave numbers (±3 $cm^{-1}$): 226.2, 297.0, 363.9, 737.3, 847.3, 1018.7 and/or 1354.3;
  a differential scanning calorimetry (DSC) peak with a $T_{onset}$ at 97° C.±2° C. measured with a heating rate of 10° C./min; and/or
  a melting point of 97° C.±2° C.

In one embodiment the novel polymorphic form of Rotigotine is characterized by two, three or four of the following X-ray powder diffraction peaks (°2θ) (±0.2): 12.04, 13.68, 17.72, 19.01, measured with a Cu—$K_\alpha$ irradiation (1.54060 Å).

In one embodiment the novel polymorphic form of Rotigotine according to the invention is characterized by peaks in its Raman spectrum at the wave numbers 297.0, 847.3 and 1018.7±3 $cm^{-1}$.

The temperatures given herein include variations of ±2° C. due to measurement inaccuracies, e.g. of a DSC experiment. The °2θ angles given herein include variations of ±0.2 due to measurement inaccuracies of the X-ray powder diffraction experiments. Finally, the wave numbers given herein include variations of ±3 $cm^{-1}$ due to measurement inaccuracies of the Raman experiments.

The present invention also provides a Rotigotine drug substance comprising at least about 5%, more preferably at least about 10%, of the novel polymorphic form of Rotigotine as defined above.

In a preferred embodiment the Rotigotine drug substance comprises at least about 50%, more preferably at least about 70%, of the novel polymorphic form (II) of Rotigotine as defined above. Most preferably substantially all or all (100%) of the Rotigotine in the Rotigotine drug substance is present in the novel polymorphic form (II). "Substantially all" is meant to refer to a Rotigotine drug substance comprising form II wherein preferably at least 80%, more preferably at least 90%, still more preferred at least 95% of the rotigotine is present as form (II).

In the context of the present application all percentages are given by weight unless otherwise indicated.

Furthermore, the present invention provides a pharmaceutical composition which comprises the novel polymorphic form (II) of Rotigotine as defined above and at least one pharmaceutically acceptable excipient.

The present invention also provides a process for producing the novel polymorphic form (II) of Rotigotine as defined above, which comprises tempering solid Rotigotine of polymorphic form (I) for at least 10 days at 40° C.

In said tempering process Rotigotine of polymorphic form (I) can either be in the dry state or in slurry state. When in slurry state, the slurry is preferably prepared in cyclohexane or ethanol.

In another preferred embodiment of the present invention the novel polymorphic form (II) of Rotigotine as defined above is quantitatively produced by spiking Rotigotine of polymorphic form (I) in slurry state with crystals of Rotigotine of polymorphic form (II) obtained from the tempering process or from ethanolic precipitation.

In another embodiment of the present invention the novel polymorphic form (II) of Rotigotine as defined above is quantitatively produced by spiking Rotigotine of polymorphic form (I) in dry state at 40° C. with crystals of Rotigotine of polymorphic form (II). The form (II) seed crystals used may be obtained from ethanolic slurry experiments, ethanolic precipitation or from another tempering process.

In an another aspect of the present invention the novel polymorphic form (II) of Rotigotine as defined above is used for treating a patient suffering from a disease sensitive to the treatment with D2 receptor agonists.

In various embodiments of the present invention the novel polymorphic form (II) of Rotigotine as defined above is used for treating a patient suffering from Parkinson's Disease, Parkinson's plus syndrome, depression, fibromyalgia or restless-legs syndrome.

BRIEF DESCRIPTION OF DRAWINGS

FIG. 1 Experimental powder X-ray diffractogram of novel polymorphic form (II) of Rotigotine FIG. 2 H-bonded polymeric (Zig-Zag) chain of Rotigotine molecules in novel polymorphic form (II) crystals FIG. 3 H-bonded polymeric (Zig-Zag) chain of Rotigotine molecules in polymorphic form (I) crystals FIG. 4 Experimental powder X-ray diffractogram of polymorphic form (I) of Rotigotine FIG. 5 Raman spectrum of novel polymorphic form (II) of Rotigotine FIG. 6 initial panel and panels 6a, 6b, and 6c depict overlay of the Raman spectra of novel polymorphic form (II) and polymorphic form (I) of Rotigotine.

FIG. 7 DSC thermogram of novel polymorphic form (II) of Rotigotine

FIG. 8 DSC thermogram of polymorphic form (I) of Rotigotine

DETAILED DESCRIPTION OF THE INVENTION

Figure 6A:
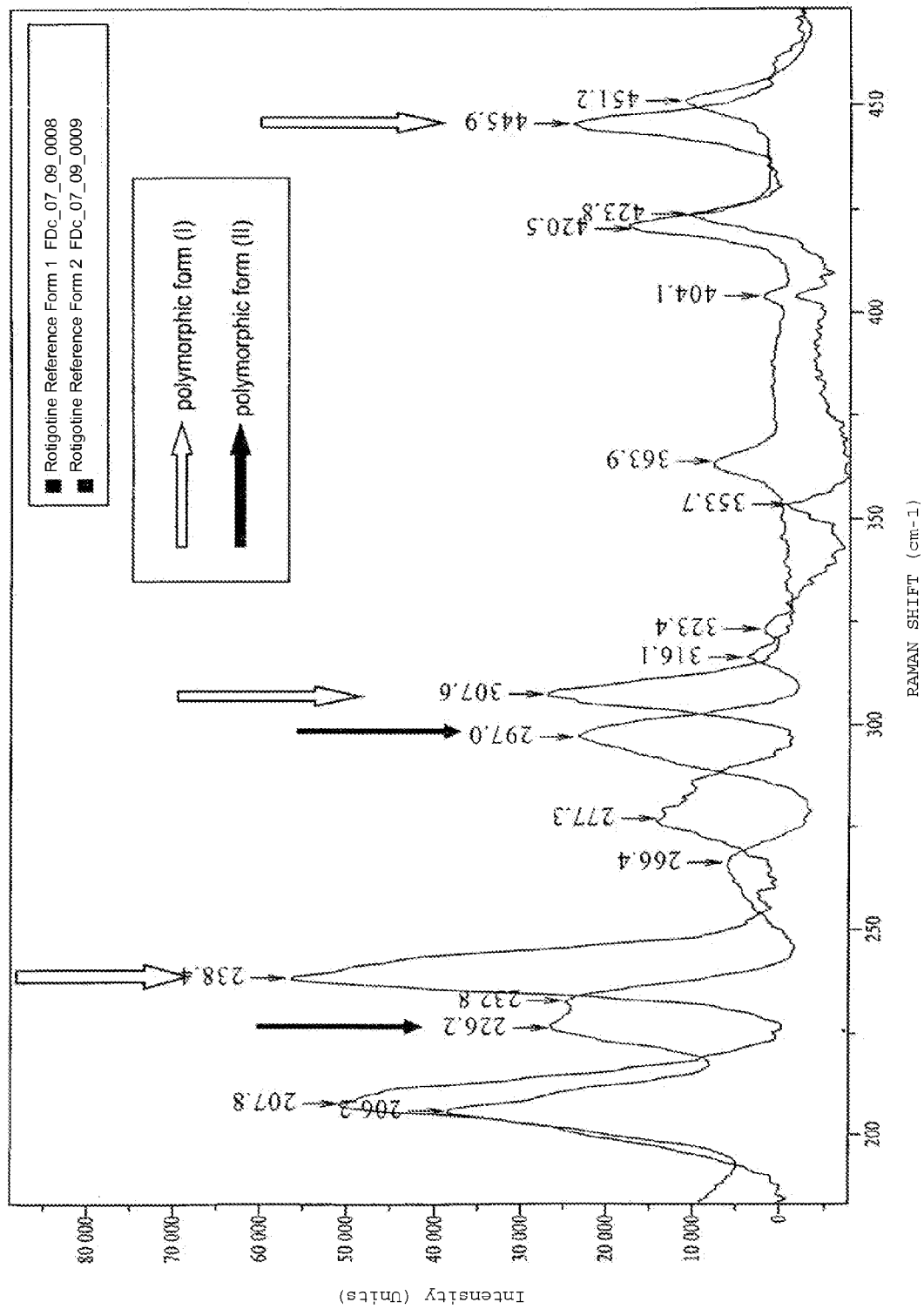

The invention relates to a novel crystalline form of ((−)-5,6,7,8-tetrahydro-6-[propyl-[2-(2-thienyl)ethyl]-amino]-1-naphthalenol), denoted herein as form II. Form II differs from form I in the structure of the crystal lattice of ((−)-5,6,7,8-tetrahydro-6-[propyl-[2-(2-thienyl)ethyl]-amino]-1-naphthalenol), and the two forms give distinctive X-ray powder diffraction (XRD) patterns, Raman Spectra and differential scanning calorimetry (DSC) thermograms.

Form I of Rotigotine is characterized by an XRD pattern comprising a peak at about 20.23±0.2 (°2θ).

Characterization of form II and distinguishing the same from form I are accomplished using techniques known to those of skill in the art. Specifically, verification that form II is present can be performed using techniques such as melting point, infrared (IR) spectroscopy, solid state nuclear magnetic resonance (SSNMR) or Raman spectroscopy. Techniques including differential scanning calorimetry (DSC) and X-ray diffraction (XRD) are also useful in distinguishing polymorphs, and specifically form II from form I. One or more of the foregoing techniques can be used to identify a polymorphic form of Rotigotine.

Form I and form II have distinctive characteristic peaks in their X-ray powder diffraction patterns as provided in FIGS. 1 and 4. At least one of these peaks, and preferably a majority of these peaks, will be present in the X-ray powder diffraction pattern for a given form.

In one embodiment of the invention the XRD pattern of form II exhibits a characteristic peak at 13.68±0.2 (°2θ), in another embodiment the XRD pattern of form II exhibits a characteristic peak at 17.72±0.2 (°2θ) and in still another embodiment the XRD pattern of form II exhibits a characteristic peak at 19.01±0.2 (°2θ). Preferably, the XRD pattern of form II exhibits characteristic peaks at 13.68 and 17.72±0.2 (°2θ). More preferably, the XRD pattern of form II can comprise peaks at 13.68, 17.72 and 19.01±0.2 (°2θ).

The novel polymorphic form (II) of Rotigotine ((−)-5,6,7,8-tetrahydro-6-[propyl-[2-(2-thienyl)ethyl]-amino]-1-naphthalenol) is characterized by a powder X-ray diffractogram comprising peaks at one or more of 12.04, 12.32, 12.97, 13.68, 17.13, 17.72, 19.01, 20.40, 20.52, 21.64, 21.96, 22.01, 22.91 and 22.96±0.2 (°2θ), measured with a Cu—K$_\alpha$ irradiation (1.54060 Å). In particular, the novel polymorphic form (II) of Rotigotine is characterized by at least one of the following X-ray powder diffraction peaks: 12.04, 13.68, 17.72 and 19.01±0.2 (°2θ), measured with a Cu—K$_\alpha$ irradiation (1.54060 Å) (FIG. 1).

The crystal lattice comparison between the novel polymorphic form (II) and polymorphic form (I) (FIGS. 2 and 3) shows that the main intermolecular hydrogen bonds are similar in the two cases:

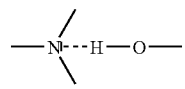

However, a drastic conformational difference is observed for the torsion angle of the thiophene ring with respect to the adjacent CH$_2$—CH$_2$ chain. It is this approximately 100° difference (torsion angle) between the two conformational polymorphs that leads to a denser packing and a change in crystal symmetry.

The results of the crystal lattice comparison are summarized in the following table:

|  |  | Form (I) | Form (II) |
| --- | --- | --- | --- |
|  |  | Crystal system | |
|  | Space group | Tetragonal P 4$_3$ | Orthorhombic P 2$_1$2$_1$2$_1$ |
| Unit cell dimension | Cell length [Å] | a 8.2030(10) b 8.2030(10) c 26.899(5) | a 8.4310(10) b 13.620(2) c 14.868(2) |
|  | Cell angle [°] | α 90 β 90 γ 90 | α 90 β 90 γ 90 |
|  | Cell volume [Å$^3$] | 1810.01 Z: 4 Z': 0 | 1707.3 Z: 4 Z': 0 |
| Density (calculated) [g/cm$^3$] |  | 1.158 | 1.227 |

These results are supported by the different solubility of the two polymorphs in EtOH. The solubility at room temperature of polymorphic form (I) of Rotigotine in EtOH is about 500 mg/mL (1:2 [w/w]), whereas the solubility of the novel polymorphic form (II) of Rotigotine in EtOH is about 60-100 mg/mL (0,6-1:10 [w/w]), i.e. the solubility of the novel polymorphic form (II) of Rotigotine in EtOH is at least five times lower than the solubility of polymorphic form (I) of Rotigotine in EtOH.

The crystallographic differences between the two polymorphic forms of Rotigotine further become apparent when comparing their X-ray diffractograms as shown in FIGS. 1 and 4.

The novel polymorphic form (II) of Rotigotine can be also characterized by its Raman spectrum (FIG. 5).

Further, differential scanning calorimetry (DSC) data reveal the difference between the two polymorphic forms of Rotigotine (FIGS. 7 and 8). Basically, the novel polymorphic form (II) of Rotigotine exhibits both a higher melting point and a higher enthalpy of fusion, and by applying the Burger-Ramberger rules, it could be stated that form (II) is thermodynamically more stable than form (I) at any temperature considered. Therefore, the two polymorphs of Rotigotine appear to be monotropically related.

Polymorph form II of Rotigotine can be further characterized and distinguished from form I by differential scanning calorimetry (DSC). A DSC thermogram of form II is provided in FIG. 7, and was obtained using DSC techniques known to those of skill in the art. One of skill in the art would readily be able to determine the conditions necessary to obtain a DSC thermogram of form II, A variety of differential scanning calorimeters are available to those of skill in the art and include the Differential-Scanning-Calorimeter from Mettler Toledo (DSC822e) using temperatures of about 25° C. to about 250° C., in particular about 30° C. to about 140° C. and temperature increases at various rates including 1° C./min, 10° C./min, 20° C./min, among other instruments and conditions. One skilled in the art would recognize that the peak positions in the DSC thermogram can vary depending upon kinetic factors such as, for example, heating rate and particle size.

The DSC thermogram of form II differs from the DSC thermogram of form I and includes a peak with a T$_{onset}$ of about 97° C.±2° C. The DSC thermogram of form I differs from the DSC thermogram of form II and includes a peak with a T$_{onset}$ of about 77° C.±2° C.

The novel polymorphic form (II) of Rotigotine can be prepared by the following processes. In these processes, "Rotigotine" means the free base, i.e., (−)-5,6,7,8-tetrahydro-6-[propyl-[2-(2-thienyl)ethyl]-amino]-1-naphthalenol.

The novel polymorphic form (II) of rotigotine can illustratively be prepared by the following processes.

(i) Preparation of the novel polymorphic form (II) of Rotigotine by tempering comprises:
  Placing Rotigotine of polymorphic form (I) in an aluthene bag
  Sealing and storing the bag at 38-40° C. for 10 days (ii) Preparation of the novel polymorphic form (II) of Rotigotine from an ethanolic slurry comprises:
  Slurrying Rotigotine of polymorphic form (I) in ethanol
  Stirring for 2 h at 50 to 150 rpm
  Optionally spiking of the ethanolic slurry of Rotigotine of polymorphic form (I) with Rotigotine of polymorphic form (II)
  Stirring for another 24 h at 50 to 150 rpm at room temperature
  Filtration of the slurry
  Drying of Rotigotine of polymorphic form (II) to constant weight The crystalline form of Rotigotine may be prepared substantially as a single polymorph, i.e., for example comprising more than 95% of form II, or may be crystallized in combination with form I or other polymorphs. In some embodiments, the crystalline form of Rotigotine comprises at least 50% of form II. In some embodiments, the crystalline form of Rotigotine comprises at least 70% of form II. In some embodiments, the crystalline form of Rotigotine comprises at least 80% of form II. In still other embodiments, the crystalline form of Rotigotine comprises at least 90% of form II.

Rotigotine polymorphic form (II) can be used as a therapeutic active substance.

When Rotigotine of novel polymorphic form (II) is used for treating a patient suffering from a disease sensitive to the treatment with D1/D2/D3 dopamine agonists, in particular D2 receptor agonists, it may be orally or parenterally administered. In general, it is parenterally administered, e.g. in the form of a transdermal therapeutic system (TTS), by injection, such as in the form of a depot suspension, by an iontophoretic device or in the form of an intranasal formulation.

Diseases that are generally treated with Rotigotine of the novel polymorphic form (II) are Parkinson's Disease, Parkinson's plus syndrome, depression, fibromyalgia and restless-legs syndrome. The respective dose will vary depending upon symptoms, age, sex, weight and sensitivity of the patients, the method of administration, time and intervals of administration and pharmaceutical preparations, etc. Hence, there is no particular limitation with respect to the dose.

Pharmaceutical preparations containing the novel polymorphic form (II) of Rotigotine such as transdermal therapeutic systems, injections or tablets etc. are prepared according to methods commonly known in the state of the art.

The invention and the best mode for carrying it out will be explained in more detail in the following non-limiting examples.

EXAMPLES

Preparation

Preparation Example 1

A sample of the polymorphic form (I) of Rotigotine batch 16208652 was placed in a small Aluthene® bag (2006 fabrication Bischoff+Klein). The sample was sealed and stored at 38-40° C. for 10 days. After this incubation time 1 g of the sample was dissolved in 2 g of EtOH, whereupon strong precipitation of form II occurred.

Preparation Example 2

5.277 kg of polymorphic form (I) of Rotigotine (batch SPM 5904) were charged in a 20 L plastic bottle and converted with 5.3 L EtOH in an ethanolic slurry. The slurry was transferred into a nitrogen flushed reactor and the plastic bottle was rinsed with further 8.1 L EtOH. The rinsing liquid was as well transferred to the reactor and the resulting suspension was stirred for 24 h at 75 rpm at room temperature. Subsequently, the crystal slurry was discharged from the reactor via a glass suction filter. The reactor was then rinsed with 2.6 L of EtOH and afterwards the rinsing liquid was used to wash the obtained filtrate. Finally, the filtrate was transferred to four tared metal sheets and dried for 43 h at 40° C. to constant weight.

In both examples the successful formation Rotigotine of polymorphic form (II) was confirmed by analytical data from DSC and XRD.

In addition, polymorphic form (I) of Rotigotine could be quantitatively transformed into polymorphic form (II) of Rotigotine in a process according to preparation example 2, when the ethanolic slurry of polymorphic form (I) was spiked with seeds of Rotigotine of polymorphic form (II).

[Characterization of the novel polymorphic form (II) of Rotigotine in comparison to polymorphic form (I) of Rotigotine]

Single Crystal X-ray Diffraction

Suitable single crystals for diffraction have been obtained by rapid evaporation of a methanol solution of rotigotine polymorphic form (II) reference batch 7769396. Single crystal X-Ray diffraction data (OXFORD Gemini R Ultra, Mo—$K_\alpha$ irradiation (0.71073 Å)) are as follows: $C_{19}H_{25}NOS$, M=315.46, Orthorhombic P $2_12_12_1$, a=8.4310 (10)Å, b=13.620(2)Å, c=14.868(2)Å, $\alpha=\beta=\gamma 90°$, V[Å$^3$]= 1707.3, Z=4, $D_c$[g/cm$^3$]=1.227, $\lambda$=1.54178 Å. Final disagreement factor R is 4%.

Cohesive forces of the crystal packing of polymorphic form (II) of Rotigotine are mainly made up of polymeric zig-zag chains of hydrogen bonds via the basic nitrogen atom (N1) and the phenol oxygen (O1).

This structure determination confirms that polymorphic form (II) is a true polymorph of Rotigotine and confirms the occurence of conformational polymorphism.

The structure determination of polymorphic form (II) of Rotigotine allows to simulate a theoretical powder X-ray pattern (Mercury 1.5) characterized by the following peaks: 8.82, 12.06, 12.34, 13, 13.7, 14.32, 17.18, 17.76, 19.04, 20.44, 22.06, 23.02, 24.26 and 27.76 (°2θ).

Experimental X-Ray Powder Diffraction

The X-ray analysis was performed on a STOE STADI-P powder diffraction System with a Cu—$K_\alpha$ irradiation (1.54060 Å), wherein it was shown that the experimental pattern of polymorphic form (II) of Rotigotine perfectly matches with its simulated powder pattern.

In accordance with embodiments of the invention, the XRD patterns of form I and form II contain peaks that are specific for each form. The XRD pattern of form II contains peaks not present in the XRD pattern of form I, and includes a peak at about 17.72±0.2 (°2θ). In another embodiment, the XRD pattern of form II differs from the XRD pattern of form I and includes a peak at about 13.68±0.2 (°2θ). In another embodiment, the XRD pattern of form II differs from the XRD pattern of form I and includes a peak at about 19.01±0.2 (°2θ). In another embodiment, the XRD pattern of form II differs from the XRD pattern of form I and includes peaks at about 17.72±0.2 (°2θ) and 19.01±0.2 (°2θ). Importantly, the XRD pattern of form II lacks a peak at about 20.23±0.2 (°2θ).

The results furthermore clearly demonstrate the difference between the two Rotigotine polymorphs (FIGS. 1 and 4). The experimental X-ray diffraction pattern of the novel polymorphic form (II) of Rotigotine is characterized by peaks at diffraction angles (°2θ) of 12.04, 12.32, 12.97, 13.68, 17.72, 19.01, 20.40, 20.52, 21.84, 21.96, 22.01, 22.91 and 22.96, whereas the experimental pattern of polymorphic form (I) is characterized by peaks at diffraction angles (°2θ) of 10.83, 12.68, 14.66, 15.32, 16.66, 16.68, 20.23, 22.67, 25.17, 25.47, 26,27, 27.75, and 29.55. Each of these peaks, either alone or in combination with others, may be taken as a basis to characterize Rotigotine of form (I) or form (II), respectively.

Raman Spectroscopy

A sample of Rotigotine was placed on a cover glass and then, based on only one crystal, the sample was focalized with 10× and 50×-WD: Raman HJY ARAMIS, laser 784.9 nm, 4×20 sec, obj. 10×+50×-WD, hole 500 μm, slit 100 μm. The acquisition was performed by 4×20 seconds with the objective 50×-WD.

Figure 6B:
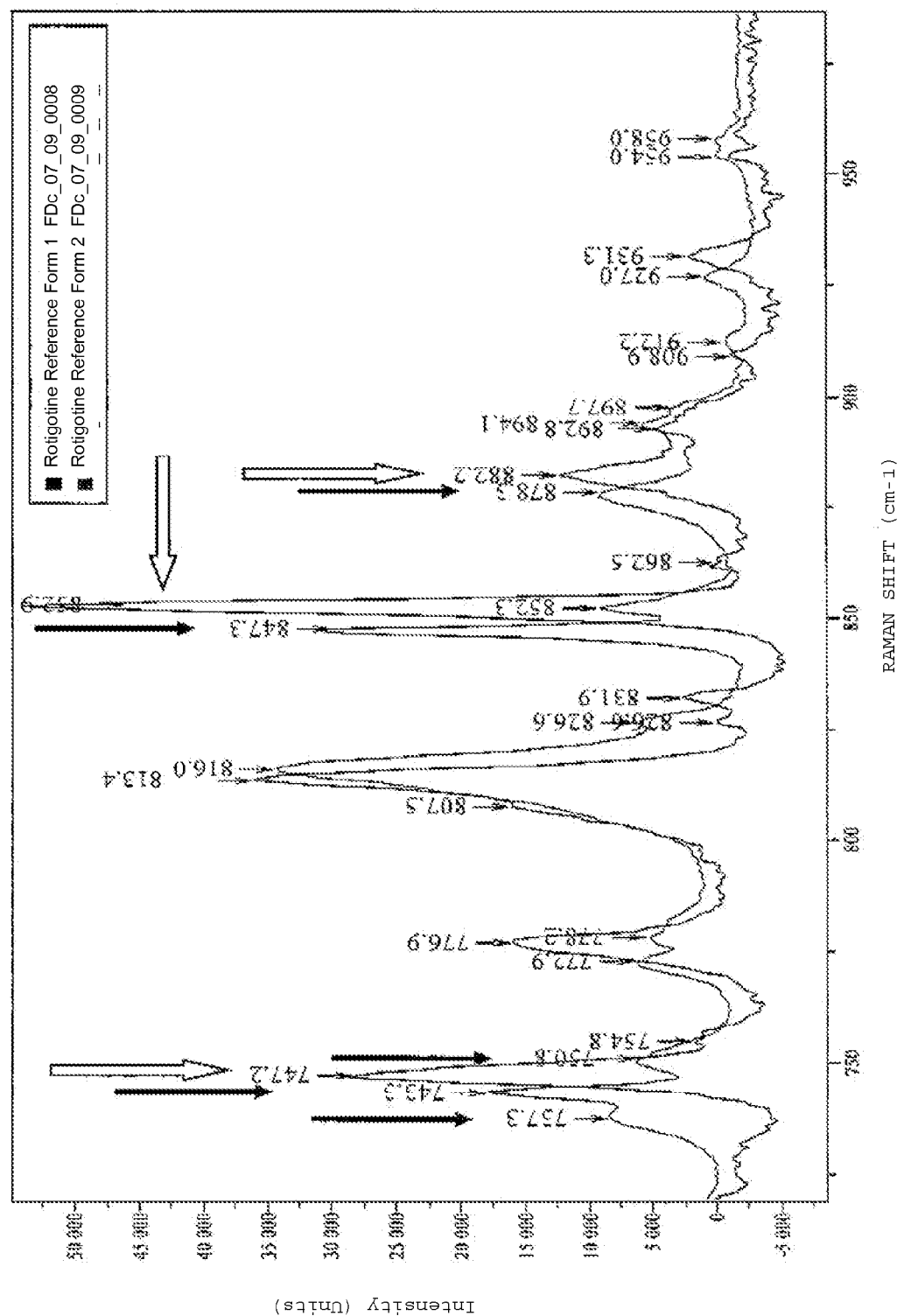
Figure 6C:
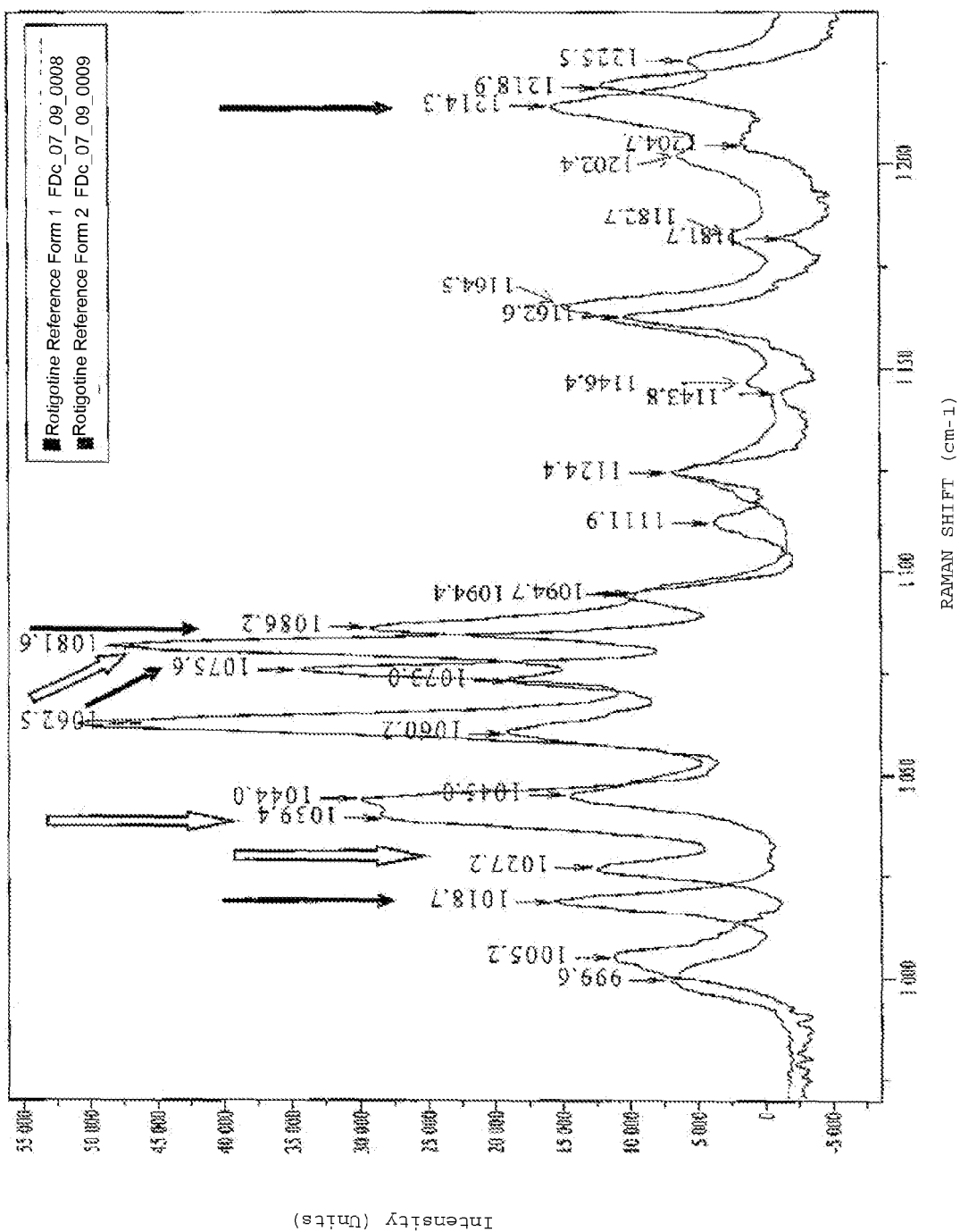

The results are shown in FIGS. 5 and 6. FIG. 5 represents the spectrum of polymorphic form (II) of Rotigotine whereas FIG. 6 shows the superimposition of batches 7769396 (reference polymorphic form (II)) and WE 11664 PS-7 (predominantly polymorphic form (I)). This overlay highlights several discriminative peaks of these two batches. The novel polymorphic form (II) of Rotigotine comprises at least one peak, preferably at least two peaks, at least three or at least four peaks at wave numbers (cm$^{-1}$) selected from 226.2, 297.0, 363.9, 710.0, 737.3, 743.3, 750.8, 847.3, 878.3, 1018.7, 1075.6, 1086.2, 1214.3, 1255.1, 1278.2, 1330.7, 1354.3 and 1448.7±3 cm$^{-1}$ whereas polymorphic form (I) exhibits characteristic peaks at wave numbers (cm$^{-1}$) of 238.4, 277.3, 307.6, 445.9, 682.6, 747.2, 882.2, 1027.2, 1039.4, 1081.6 and 1324.3±3 cm$^{-1}$. The novel polymorphic form (II) of Rotigotine ((−)-5,6,7,8-tetrahydro-6-[propyl-[2-(2-thienyl)ethyl]-amino]-1-naphthalenol) is characterized by a Raman spectrum comprising at least one peak, preferably at least two, at least three or at least four peaks at wave numbers (cm$^{-1}$) selected from 710.0, 737.3, 743.3, 847.3, 1018.7, 1214.3, 1278.2, 1354.3±3 cm$^{-1}$. In particular, the novel polymorphic form (II) of Rotigotine is characterized by at least one of the following peaks: 226.2, 297.0, 363.9, 737.3, 847.3, 1018.7 and 1354.3±3 cm$^{-1}$.

Differential Scanning Calorimetry (DSC)

Thermal behavior investigations of Rotigotine of polymorphic form (I) (batch 1608726) and of polymorphic form (II) (batch 7769396) were performed on a Mettler Toledo DSC system and on a TA instrument (Q-1000). The analyses were carried out with a heating rate of 10° C./min in pierced aluminum crucibles in a temperature range from 30° C. to 140° C.

The results are summarized in FIG. 7 and FIG. 8. The DSC thermogram of the novel polymorphic form (II) exhibits an endothermic peak with a $T_{onset}$ at 97±2° C. and a $T_{peak}$ at 98° C.±2° C., whereas the onset of the endothermic peak of polymorphic form (I) is at 77±2° C. under the same conditions. For both polymorphs only one single peak could be observed in their thermograms, indicating said polymorphs being free of any impurities of the respective other polymorph, with respect to DSC sensitivity.

In sum, the two polymorphic forms of Rotigotine can be differentiated by their respective melting point and their respective enthalpy of fusion. Both are higher for the novel polymorphic form (II) and by applying the Burger-Ramberger rules, it could be demonstrated that polymorphic form (II) is thermodynamically more stable than polymorphic form (I) at all considered temperatures. Therefore, the two polymorphs of Rotigotine are most probably monotropically related.

The melting point of the novel polymorphic form (II) of Rotigotine can also be measured with the capillary method (in an oil/water bath with a magnifier) or with a Kofler Hotbench.

The invention claimed is:

1. A pharmaceutical composition comprising at least 5% rotigotine polymorphic form (II) and at least one pharmaceutically acceptable excipient, wherein the rotigotine polymorphic form (II) is characterized by having at least one parameter selected from the group consisting of:
   an X-ray powder diffraction spectrum comprising at least one peak at the following °2θ angles (±0.2): 12.04, 13.68, 17.72, 19.01;
   a Raman spectrum comprising at least one peak at the following wave numbers (±3 cm$^{-1}$): 226.2, 297.0, 363.9, 737.3, 847.3, 1018.7, 1354.3 cm$^{-1}$;
   a DSC peak with a $T_{onset}$ at 97° C.±2° C. measured with a heating rate of 10°/min; and
   a melting point of 97° C.±2° C.

2. The pharmaceutical composition according to claim 1 which is in form of a transdermal therapeutic system.

3. A method for treating a patient suffering from a disease sensitive to treatment with D2 receptor agonists, the method comprising administering to the patient rotigotine polymorphic form (II), wherein the rotigotine polymorphic form (II) is characterized by having at least one parameter selected from the group consisting of:
   an X-ray powder diffraction spectrum comprising at least one peak at the following °2θ angles (±0.2): 12.04, 13.68, 17.72, 19.01;
   a Raman spectrum comprising at least one peak at the following wave numbers (±3 cm$^{-1}$): 226.2, 297.0, 363.9, 737.3, 847.3, 1018.7, 1354.3 cm$^{-1}$;
   a DSC peak with a $T_{onset}$ at 97° C.±2° C. measured with a heating rate of 10°/min; and
   a melting point of 97° C.±2° C. wherein the disease is selected from the group consisting of Parkinson's Disease, Parkinson's plus syndrome, depression, fibromyalgia and restless-legs syndrome.

4. The pharmaceutical composition of claim 1 comprising at least 50% rotigotine polymorphic form (II).

5. The pharmaceutical composition of claim 4, wherein substantially all of the rotigotine present is polymorphic form (II).

* * * * *

UNITED STATES PATENT AND TRADEMARK OFFICE
CERTIFICATE OF CORRECTION

PATENT NO. : 8,592,477 B2  
APPLICATION NO. : 12/744989  
DATED : November 26, 2013  
INVENTOR(S) : Hans-Michael Wolff et al.

Page 1 of 1

It is certified that error appears in the above-identified patent and that said Letters Patent is hereby corrected as shown below:

In the Specification

Column 4, line 38, replace "21.64" with --21.84--.

Column 5, line 50, replace "II," with --II.--.

Column 8, line 13, replace "26,27" with --26.27--.

Column 9, line 21, replace "97° C.±2° C." with --97°C ± 2°C--.

Column 9, line 23, replace "97° C.±2° C." with --97°C ± 2°C.--.

Column 10, line 13, replace "97° C.±2° C." with --97°C ± 2°C--.

Column 10, line 15, replace "97° C.±2° C." with --97°C ± 2°C,--.

Signed and Sealed this  
Seventeenth Day of June, 2014

Michelle K. Lee  
*Deputy Director of the United States Patent and Trademark Office*

UNITED STATES PATENT AND TRADEMARK OFFICE
CERTIFICATE OF CORRECTION

| | | |
|---|---|---|
| PATENT NO. | : 8,592,477 B2 | Page 1 of 1 |
| APPLICATION NO. | : 12/744989 | |
| DATED | : November 26, 2013 | |
| INVENTOR(S) | : Wolff et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 400 days.

Signed and Sealed this
Eleventh Day of November, 2014

Michelle K. Lee
*Deputy Director of the United States Patent and Trademark Office*